United States Patent [19]

Peterson et al.

[11] Patent Number: 5,256,640
[45] Date of Patent: Oct. 26, 1993

[54] GALLSTONE MITIGATION BY NUTRIENT STIMULATED GALLBLADDER CONTRACTION

[75] Inventors: Francis J. Peterson, Apple Valley, Minn.; Louis J. Arrone, Pelham Manor, N.Y.

[73] Assignee: Sandoz Ltd., Basel, Switzerland

[21] Appl. No.: 768,142

[22] Filed: Sep. 30, 1991

[51] Int. Cl.$^5$ ............... A61K 37/18; A61K 31/70; A61K 31/715; A61K 31/525
[52] U.S. Cl. .................................. 514/2; 514/23; 514/52; 514/53; 514/54; 514/251; 514/474; 514/558; 514/726; 514/877; 424/600
[58] Field of Search ............. 424/195.1, 600; 514/1, 514/2, 23, 53, 54, 558, 52, 251, 474, 726, 877

[56] References Cited

U.S. PATENT DOCUMENTS 4,572,915  2/1986  Crooks ........................... 514/458

*Primary Examiner*—John W. Rollins
*Attorney, Agent, or Firm*—Robert S. Honor; Melvyn M. Kassenoff; Carl W. Battle

[57] ABSTRACT

Nutritional supplements and methods of use of the supplements to maximally stimulate gallbladder contraction in patients undergoing rapid weight loss, to prevent the build up of bilary sludge and/or gallstones.

15 Claims, No Drawings

GALLSTONE MITIGATION BY NUTRIENT STIMULATED GALLBLADDER CONTRACTION

BACKGROUND OF THE INVENTION

This application relates to nutritional supplement compositions and methods of the use of the nutrition supplements to maximally stimulte contraction of the gallbladder in patients undergoing rapid weight loss, for the purpose of preventing the build up of biliary sludge and/or gallstones.

Gallbladder disease is widespread and occurs in an estimated 20 million Americans, with over 2.5 billion dollars spent annually on surgical interventions. The etiology of gallbladder disease is complex and incompletely understood. Several key factors appear to interact for gallstone formation including obesity, biliary stasis, biliary lithogenicity and nucleation of bile solutes. The prevention or mitigation of all, or several of these factors may be helpful in minimizing the need for surgery and decrease the incidence and severity of this national health issue.

Recent clinical trials have evaluated several different preventative treatments including oral chemolysis with ursodiol, which decreases the lithogenicity of the bile; cholecystokinin infusion, which decreases stasis in long-term total parenteral nutrition patients (TPN); and aspirin or anti-inflammatory drugs, which appear to decrease nucleation factors. These approaches each have shown a significant impact in decreasing the incidence of sludge as well as stone formation. Other clinical studies, have shown the development of small cholesterol gallstones in some obese patients undergoing rapid weight loss. These findings were associated with favorable conditions for gallstone formation: an increase in cholesterol saturation, an increase in nucleation factors, and an increase in biliary sludge. The increase in biliary sludge has also been reported consistently in TPN patients prior to the development of gallstones.

One logical strategy for minimizing sludge development is frequent stimulation of gallbladder contraction in order to minimize gallbladder stasis. It is hypothesized that this event may override the importance of the other key factors needed for stone formation and that frequent contraction may prevent the build up of sludge in the gallbladder, at least during periods of caloric restriction. Since gallbladder contraction is under hormonal, as well as vagal control, and since the hormonal control is regulated significantly by diet, it would seem justified to investigate the use of dietary formulations that would contract the gallbladder maximally and frequently for the purpose of preventing build up of biliary sludge.

The exact pathogenesis of cholesterol gallstone development remains unresolved. It is hypothesized that several key factors are essential for the ultimate formation of the stones. Lithogenic bile, saturated with either cholesterol or calcium bilirubinate is an important prerequisite. Once the concentration of either critical compound has exceeded its ability to be solubilized by the biliary phospholipids and bile acids, precipitation or crystallization may occur. However, cholesterol supersaturation of bile alone does not necessarily lead to gallstone formation. A second critical factor for stone development is the nucleation of bile solutes which allows these key compounds, cholesterol or calcium bilirubinate, to crystalize or granulize within the gallbladder. The secretion of mucus glycoproteins by the gallbladder epithelium has been reported to play a pivotal role in the initiation of this process. It has been suggested that these nucleation factors appear to be influenced by the concentration of arachiodonic acid in the biliary phospholipid matrix, by the concentration of deoxycholic acid as well as by the eiconsanoids derived from omega-6 fatty acids. A third critical element is gallbladder stasis. It is hypothesized that the stasis may allow the other important factors, lithogenicity and nucleation, the opportunity to initiate microcrystals in the sludge and set the ground work for continued stone growth. Recent clinical trials have suggested that the prevention of this final key element may be powerful enough to minimize the importance of the prior two key factors. However, no totally conclusive data are present in the literature citing defective gallbladder motor function creating biliary stasis as the critical factor in patients that have gallstones. In fact, data have been reported that gallstone patients have increased, dedreased or no change in motor function when compared to control subjects.

A very critical factor in the development of gallstones, that lends itself to be influenced by dietary factors, is inadequate gallbladder contraction and biliary stasis. The contraction and subsequent emptying of the gallbladder is under both vagal and hormonal control. Truncal vagotomy has been shown to significantly improve the composition of biliary lipids and bile acid pool sizes, suggesting that vagal tone does little to contribute to gallstone predisposition by changing the CSI. Further studies on the effect of cholinergic changes on gallbladder emptying have shown the CCK-stimulated gallbladder emptying was increased in patients whicfh had undergone vagotomy as compared to non-vagotomized control patients.

However, the effects of vagotomy on gallbladder motor function are still controversial since some investigations report a decrease or no effect of cholinergic disruption in gallbladder emptying. The gastrointestinal hormone, cholecystokinin (CCK), then becomes a very important modulator of gallbladder contraction and emptying. The release of this hormone can be significantly stimulated by specific dietary nutrients, in particular dietary protein (animo acids and or peptides) and/or fat. The quantity of CCK that is released directly correlates with the degree of gallbladder contraction. It is hypothesized that the greater the degree of gallbladder contraction with a single meal stimulus, the better the chance to minimize the impact of gallbladder stasis.

The importance of gallbladder stasis in the development of gallstones has been described by a number of investigators. The prevention of gallbladder stasis, in the cholesterol-fed prairie dog model, various methods including sphincterotomy, a protein-fat nasal infusion, or else by daily CCK injection have all been shown to prevent gallstone formation. In the latter study, all patients on TPN therapy developed sludge after six weeks of treatment. However, the oral refeeding of these patients over a four week period completely eliminated all the biliary sludge detectable by ultrasonography. The former trial randomized previously treated TPN patients with no gallbladder sludge or stones into two groups; one group received a daily infusion of CCK while the second group received a daily infusion of saline. After an unspecified period of CCK or saline infusion, none of the patients treated with CCK developed any detectable sludge or stones while five out of eight patients treated with saline had developed biliary sludge. Unfortunately, neither CSI or the nucleation times were measured in this study so that it is not certain how these key factors may have been influenced by frequent gallbladder contraction.

During low calorie dieting for substantial weight loss, resultant poor stimulation of gallbladder emptying because of inadequate fat and/or protein to stimulate CCK release might facilitate cholesterol nucleation, gallbladder sludge formation and/or stone growth and retention with subsequent increased rate of gallstone formation. This is an especially important concept since an increase in biliary cholesterol saturation index has not been consistently reported to occur in obese subjects during rapid weight loss. However, a recent abstract in which the gallbladders of weight-reducing obese patients were contracted by CCK infusion every three to seven days for 28 days reported that the CSI and nucleation time did not change significantly over time and the bile became more lithogenic. However, this study did not measure fasting or residual gallbladder volume so it is not certain if gallbladder contraction changed over time.

There is conflicting data in the literature regarding the effect of obesity on gallbladder motility. it has been shown in obese diabetic and non-diabetic patients that there was no correlation between the degree of obesity and gallbladder emptying in response to cholecystokinin. These results also suggest that obese subjects do not have a impaired CCK release in response to a maximal liquid meal stimulus. These data do conflict with other data where it is reported larger gallbladder volumes in obese subjects and a reduced percent gallbladder emptying in response to a solid meal stimulus when compared to normal weight subjects. However, gallbladder volumes in both normal weight and obese subjects in this latter study were greater than two times the values found in the previous study, and substantially higher than the majority of published values. Differences in percent emptying between the two studies may relate to differences in the nature of the emptying stimuli (solid complex meal versus CCK infusion) or to the delivery of the stimulus to the duodenum mediated by the rate of gastric emptying.

Thus, there is a need to find a way, such as via a nutritional formulation, to maximally contract the gallbladder on a daily basis in obese patients undergoing caloric restriction for weight loss to prevent or mitigate the formation of gallstones. All weight reducing diets or calorically restricted diets at present, attempt to significantly decrease the amount of dietary fat consumed per day by the patient undergoing therapy. Excessive intake of dietary fat and total calories is considered by most health professionals to be the major nutrient imbalance in our diet that precipitates the disease of obesity. As a result of this concern, the health professionals attempt to restrict the amount of dietary fat consumed daily and also the amount of dietary fat consumed at any one eating occasion. In fact, most diet phases drastically reduce the amount of dietary fat consumed at a very important meal, breakfast, by encouraging the use of cereal on grain products with skim milk. The gallbladder is distended maximally or contains the greatest volume of bile in the morning after an overnight fast. Furthermore, the gallbladder empties to the greatest extend when contracted maximally in the morning. Thus, it becomes very important to contract the gallbladder maximally in the morning and to use a nutritional composition, in the reduced calorie diet plan, that contains a significant quantity of dietary fat and protein. It can be seen from the previous review, that the obese patient undergoing weight reduction could be at an increased risk of developing gallbladder abnormalities (sludge or stress) if the gallbladder is not effectively evacuated or contracted on a daily basis. Thus, the nutritional compostion of the reduced calorie diet plus the time at which the food is consumed, could be an important concept that has not been fully appreciated in mitigating gallbladde disease.

SUMMARY OF THE INVENTION

This invention provides nutritional formulations to maximally contract the gallbladder on a daily basis in patients, e.g., obese patients, undergoing weight reduction or weight maintenance using any dietary plan involving caloric restriction. The patient would consume the nutritional formulations in either a solid or liquid state, containing a minimum caloric value, at a specified, daily time to maximally contract the gallbladder.

The nutritional formulations of this invention contain on a per serving basis from about 20 gms to about 35 gms, preferably 26 gms of protein; from about 5 gms to about 15 gms, preferably 10 gms of fat; and from about 6 gms to about 15 gms, preferably Il gms of carbohydrate. The formulations provide a caloric content of about 300 Kcal per serving.

The fat source is primarily composed of long chain fatty acids of from 12-24 carbons. Suitable sources for such fatty acids include canola oil, corn oil, safflower oil, soy bean oil, peanut oil, palm kernal oil, fish oil, perilla oil and the like. The type of protein to be used in the formula desirably may be a protein of a high biological value such as those proteins contained in egg or milk products. Suitable protein sources include casinates, whey protein and egg albumin or mixtures thereof. Suitable carbohydrate sources include maltodextrins, polydextrose, sucrose, fructose, high fructose, corn syrup, corn syrup solids, honey and lactose. Dietary fiber may also be included in the formulations at a level of less than 3 g per serving. Essential vitamins and mineral at least 25% of the USRDA are also desirable in the formulations.

DESCRIPTION OF THE PREFERRED EMBODIMENTS

It has been found that the formulations of this invention when consumed as a liquid or as a liquid and a solid bar or possibly two solid bars plus a liquid, can effectively contract the gallbladder in weight reducing or weight stable patients.

The following is an example of the formulations of the present invention in a clinical trial. Lean and obese patients were recruited and gallbladder emptying was studied after an ovenight fast. Serial measurements of gallbladder volume were made with real-time scanning by an ATL ultrasound system, using a 5 MHZ annular array transducer. Mean fasting volume in individual patients on four separate occasions had a mean coefficient of variation of 20%. Volume was calculated by the sum of cylinders technique. snce there was no significant difference between normal BMI and high BMI or male or female subjects in terms of gallbladder emptying, all patients were combined in the final analysis.

Table 1 describes the characteristics of the study population.

TABLE 1

| PARAMETER | NORMAL BMI | HIGH BMI |
|---|---|---|
| Age (yrs) | 28 ± 3 | 37 ± 1 |
| Sex | 3M/4F | 3M/4F |
| Weight (Kgs) | 68.6 ± 5.5 | 100.9 ± 6.8 |
| BMI* | 22 ± 1 | 36 ± 1 |

*BMI = classification of obesity $\frac{\text{weight Kg}}{\text{Height M}^2}$

Table 2 describes the gallbladder emptying of various meal stimuli. The liquid max meal stimuli, formulated from previously published studies, contracted the gallbladder. The percent contraction is considered to be 100% for the purpose of the following discussion, since the gallbladder never completely empties. The liquid min meal 1 was a poor stimulus for gallbladder emptying and resulted in a significantly diminished contraction (64% of the max meal). This liquid min meal 1 is similar in composition to that formulation used prior art clinical trial where obese patients losing weight on a VLCD. In this trial, patients that had no ultrasongraphically detectable sludge or stress at baseline, developed a 25% incidence in gallbladder abnormalities at 8 weeks. It is hypothesized that the degree of gallbladder contraction, similar to that found with the liquid min meal 1 stimuli, may have been a participating factor in the development of the gallbladder disease. Thus a dose response curve was established to find the minimum level of dietary fat needed to contract the gallbladder to a degree similar to the liquid max meal. Dietary fat seemed to elicit the greatest response to gallbladder contractions and became the primary focus of the research. Table 2 gives a comparison of the percent gallbaldder emptying by the various liquid meal stimuli plus other dietary ingredients. When dietary fat was needed at a level of 10 g per serving, the gallbladder emptied to same degree as the liquid max meal. The consumption of the formulation liquid min meal 2 in a larger volume (up to 16 oz fluid instead of 8 oz of fluid) did not impair the ability of the gallbladder to contract. However, the addition of total dietary fiber (6 g) did decrease the percent the gallbladder emptied, probably as a result of delayed gastric emptying.

Also seen in Table 2 is the T1/2, the time required for the gallbladder to empty 50% of its initial volume. The meal stimuli that contract the gallbladder least effecively, seem to have a prolonged T1/2. Conversely, the stimuli that maximally contract the gallbladder, seem to empty the gallbladder in the shortest period of time. The meaning of a significant change in the T1/2 is not completely understood at this time, but it is assumed that a short T1/2 is important, for the greatest impact.

The long standing theory of formula diets used for weight loss or weight maintenance was that the diet should contain as little fat as possible. Most prior art formula diets were manufactured with the concept that the least amount of dietary fat made the product more desirable. Thus, the addition of dietary fat in the formulation of this invention are an advance over the prior art formulation.

Most formula diets are consumed as a liquid, however, patients continue to request solid food during weight loss phase. The consumption of a breakfast bar containing (5 g of fat, 14 g of protein and 11 g carbohydrate) in addition to the liquid min meal 2, containing a similar composition, resulted in equivalent gallbladder contraction to that found with the liquid max meal. Thus, the gallbladder can be maximally contracted with the simultaneous ingestion of a specifically formulated liquid and a bar.

Studies have suggested that individual amino acids, such as phenylalanine and tryptophan may stimulate the contraction of the gallbladder by releasing endogenous hormones. As seen in Table 2, the addition of 2 g of phenylalanine to the liquid min meal, did not result in any additional contraction of the gallbladder.

TABLE 2

| Meal Stimuli a,b | Gallbladder Emptying % c | Percent of Max | T ½(Min) d |
|---|---|---|---|
| Liquid Max Meal (23 gP, 22 gF, 40 gCHO) | 73.9 ± 13.4 | 100 | 16 |
| Liquid Min Meal 1 (14 gP, < 1 gF, 6 gCHO) | 47.4 ± 15.7 | 64 | 26 |
| Liquid Min Meal 1 + 2.6 g Fat | 63.2 ± 3.7 | 86 | 20 |
| Liquid Min Meal 1 ± 4.0 g Fat | 63.0 ± 12.5 | 86 | 19 |
| Liquid Min Meal 1 + 10 g Fat | 73.4 ± 6.2 | 100 | 20 |
| Two Liquid Min Meal 2 + 6 gTDF (14 g p, 5 gF, 11 g CHO) plus 16 oz fluid | 52.1 ± 4.3 | 71 | 18 |
| Two Liquid Min Meal 2 (plus 16 oz fluid) | 70.1 ± 3.1 | 95 | 19 |
| Liquid Min Meal 2 + Solid Min Meal 2 | 73.7 ± 8.1 | 100 | 18 |
| Liquid Min Meal 1 + 20 g Fat | 77.4 ± 10.2 | 105 | 16 |
| Liquid Min Meal 1 + 2 g Ph.Al. | 49.7 ± 7.8 | 67 | 24 | a All Stimuli consumed in or with 8 oz fluid
c Mean ± S.E. Percent volume of the total gallbladder that is emptied with the stimuli
b All Stimuli given to at least 6 patients
d T ½ refers to the time required to empty one half of the initial gallbladder volume.

MACRONUTRIENT FORMULATION OF TABLE 2

| | Liquid Min Meal 1 | |
|---|---|---|
| Protein (14 gms) | Calcium casinate | 11.2 gms |
| | Egg albumin | 2.8 gms |
| Fat (less than 1 gm) | Partionally hydrogenated Soybean oil | |
| Carbohydrate (6 gm) | Maltodextrin | 1 gm |
| | Fructose | 5 gm |
| | Liquid Min Meal 2 | |
| Protein (28 gm) | Calcium casinate | 22.4 gm |
| | Whey protein concentrate | 5.6 gm |
| Fat (10 gm) | canola oil | |
| Carbohydrates (11 gms) | Maltodextrin | 6 gm |
| | Fructose | 5 gm |
| | Solid Min Meal 2 | |
| Protein (15 gm) | soy protein isolate | 7.5 gm |
| | calcium casinate | 7.5 gm |
| Fat (5 gm) | peanut oil | 3 gm |
| | soybean oil | 2 gm |
| Carbohydrate (11 gm) | polydextrose | 4 gm |
| | fructose | 3 gm |
| | high fructose corn syrup | 1 gm |
| | corn syrup solid | 1 gm |
| | maltodextrose | 1 gm |
| | honey | 1 gm |

MICRONUTRIENT FORMULATION OF TABLE 2

| NUTRIENT | | 0.8 SERVING | % US RDA |
|---|---|---|---|
| vitamin A | IU | 1000 | 100 |
| vitamin D | IU | 80 | 100 |
| vitamin E | IU | 6.0 | 100 |
| vitamin C | mg | 18 | 150 |
| folic acid | mg | 0.08 | 100 |
| thiamine | mg | 0.45 | 150 |
| riboflavin | mg | 0.52 | 150 |
| niacin | mg | 4.0 | 100 |
| vitamin B6 | mg | 0.6 | 150 |
| vitamin B12 | mcg | 1.2 | 100 |
| biotin | mg | 0.06 | 100 |

TABLE 2-continued

| | | | |
|---|---|---|---|
| pantothenic acid | mg | 2.0 | 100 |
| calcium | g | 0.2 | 100 |
| phosphorus | g | 0.2 | 100 |
| iodine | mcg | 30 | 100 |
| iron | mg | 3.6 | 100 |
| magnesium | mg | 80 | 100 |
| copper | mg | 0.4 | 100 |
| zinc | mg | 3.0 | 100 |
| vitamin K | mcg | 20 | ** |
| choline | mg | 20 | ** |
| potassium | mg | 470 | ** |
| sodium | mg | 230 | ** |
| chloride | g | 0.4 | ** |
| manganese | mg | 0.8 | ** |
| selenium | mcg | 30 | ** |
| chromium | mcg | 30 | ** |
| molybdenum | mcg | 60 | ** |

*Percentage of U.S. Recommended Daily allowances (U.S. RDA).
**No U.S. RDA Established.

What is claimed is:

1. A method of contracting the gallbladder to prevent the buildup of biliary sludge and gallstones which comprises administering a nutritional supplement comprising from about 20 g to about 35 g of protein; from about 5 g to about 15 g of fat; and from about 6 g to about 15 g of carbohydrate per daily serving.

2. The method according to claim 1 wherein the amount of protein is about 26 g; the amount of fat is about 10 g; and the amount of carbohydrate is about 11 g.

3. The method according to claim 1 or 2 wherein the protein is derived from high biological value protein, and the fat is derived from a fat source containing long chain fatty acids.

4. The method according to claim 3 wherein the protein source is casinates, whey protein, egg albumin or mixtures thereof, and the fat source is long chain fatty acids from 12 to 24 carbons.

5. The method according to claim 4 wherein the fat source is corn oil, safflower oil, canola oil, fish oil, soy bean oil, peanut oil, palm kernel oil or perilla oil.

6. The method according to claim 5 wherein the carbohydrate source is selected from the group consisting of maltodextrins, polydextrose, sucrose, fructose, high fructose corn syrup, corn syrup solids, honey and lactose.

7. The method according to claim 6 wherein said nutritional supplement additionally contains at least 25% of the U.S. recommended daily allowances of all essential vitamins and minerals.

8. The method according to claim 7 wherein the nutritional supplement is administered twice daily, once in the morning and once in the evening.

9. A nutritional supplement for contracting the gallbladder to prevent the buildup of biliary sludge and gallstones which comprises from about 20 g to about 35 g of protein; from about 5 g to about 15 g of fat; and from about 6 g to about 15 g of carbohydrate per daily serving.

10. The nutritional supplement according to claim 9 wherein the amount of protein is about 26 g; the amount of fat is about 10 g; and the amount of carbohydrate is about 11 g.

11. The nutritional supplement according to claim 9 or 10 wherein the protein is derived from high biological value protein, and the fat is derived from a fat source containing long chain fatty acids.

12. The nutritional supplement according to claim 11 wherein the protein source is casinates, whey protein, egg albumin or mixtures thereof, and the fat source is long chain fatty acid of from 12 to 24 carbons.

13. The nutritional supplement according to claim 12 wherein the fatty acid source is corn oil, safflower oil, canola oil, soy bean oil, peanut oil, palm kernel oil, fish oil, or perilla oil.

14. The nutritional supplement according to claim 12 wherein the carbohydrate source is selected from the group consisting of maltodextrins, polydextrose, sucrose, fructose, high fructose corn syrup, corn syrup solids, honey and lactose.

15. The nutritional supplement according to claim 12 wherein said nutritional supplement additionally contains at least 25% of the U.S. recommended daily allowances of all essential vitamins and minerals.

* * * * *